United States Patent
Bernard

(10) Patent No.: US 11,844,418 B2
(45) Date of Patent: Dec. 19, 2023

(54) TOOTHBRUSH WITH TOOTHPASTE PELLETS

(71) Applicant: Austin Bernard, Laguna Niguel, CA (US)

(72) Inventor: Austin Bernard, Laguna Niguel, CA (US)

(*) Notice: Subject to any disclaimer, the term of this patent is extended or adjusted under 35 U.S.C. 154(b) by 55 days.

(21) Appl. No.: 17/450,911

(22) Filed: Oct. 14, 2021

(65) Prior Publication Data

US 2022/0110440 A1    Apr. 14, 2022

Related U.S. Application Data

(60) Provisional application No. 63/091,902, filed on Oct. 14, 2020.

(51) Int. Cl.

| | | |
|---|---|---|
| *A46B 11/00* | (2006.01) | |
| *A46B 9/04* | (2006.01) | |
| *A46B 15/00* | (2006.01) | |
| *A61K 8/02* | (2006.01) | |

(Continued)

(52) U.S. Cl.
CPC ............ *A46B 11/0068* (2013.01); *A46B 5/00* (2013.01); *A46B 9/04* (2013.01); *A46B 11/0062* (2013.01); *A46B 11/0089* (2013.01); *A46B 15/0095* (2013.01); *A61K 8/0216* (2013.01); *A61Q 11/00* (2013.01); *A46B 2200/1066* (2013.01); *A61K 2800/222* (2013.01)

(58) Field of Classification Search
CPC ............ A46B 11/0068; A46B 11/0062; A46B 11/0089; A46B 11/00; A46B 11/0006; A46B 5/00; A46B 9/04; A46B 15/0095; A46B 2200/1066; A61K 8/0216; A61K 2800/222; A61Q 11/00
USPC ........................................ 15/104.94
See application file for complete search history.

(56) References Cited

U.S. PATENT DOCUMENTS

| | | | |
|---|---|---|---|
| 10,827,824 B1* | 11/2020 | Ferzli ..................... | A45D 27/04 |
| 2006/0159509 A1* | 7/2006 | Grez ...................... | A61C 17/22 |
| | | | 401/123 |

(Continued)

FOREIGN PATENT DOCUMENTS

| | | | |
|---|---|---|---|
| FR | 2606615 A1 * | 5/1988 | |
| FR | 2646068 A1 * | 10/1990 | |

(Continued)

*Primary Examiner* — Brian D Keller
*Assistant Examiner* — Robert C Moore
(74) *Attorney, Agent, or Firm* — Thomas J. Oppold; Larkin Hoffman; Daly & Lindgren, Ltd.

(57) ABSTRACT

A toothbrush having a handle portion, a shank portion and a head portion. A channel extends longitudinally through the handle portion, the shank portion and terminates in the head portion. The channel is sized to slidably receive one or more toothpaste pellet formulated to effervesce when exposed to water or saliva. An aperture extends transverse through the head portion providing fluid communication into the channel. A one-way gate is disposed within the channel permitting a toothpaste pellet to pass into the head portion, and to prevent the toothpaste pellet from passing out of the head portion. A handle cap is removably attached to a lower end of the handle portion. The head portion and shank portion may be received within a head cap that removably attaches to the handle portion.

10 Claims, 2 Drawing Sheets

(51) Int. Cl.
*A61Q 11/00* (2006.01)
*A46B 5/00* (2006.01)

(56) References Cited

U.S. PATENT DOCUMENTS

| | | | |
|---|---|---|---|
| 2009/0119859 A1* | 5/2009 | Podolsky | A46B 11/002 401/129 |
| 2015/0257522 A1* | 9/2015 | Boyke | A46B 11/00 132/311 |
| 2020/0229583 A1* | 7/2020 | Pimenta | A46B 9/04 |

FOREIGN PATENT DOCUMENTS

| WO | WO-2016028259 A1 * | 2/2016 | ........... A46B 11/002 |
|---|---|---|---|
| WO | WO-2018051219 A1 * | 3/2018 | |

* cited by examiner

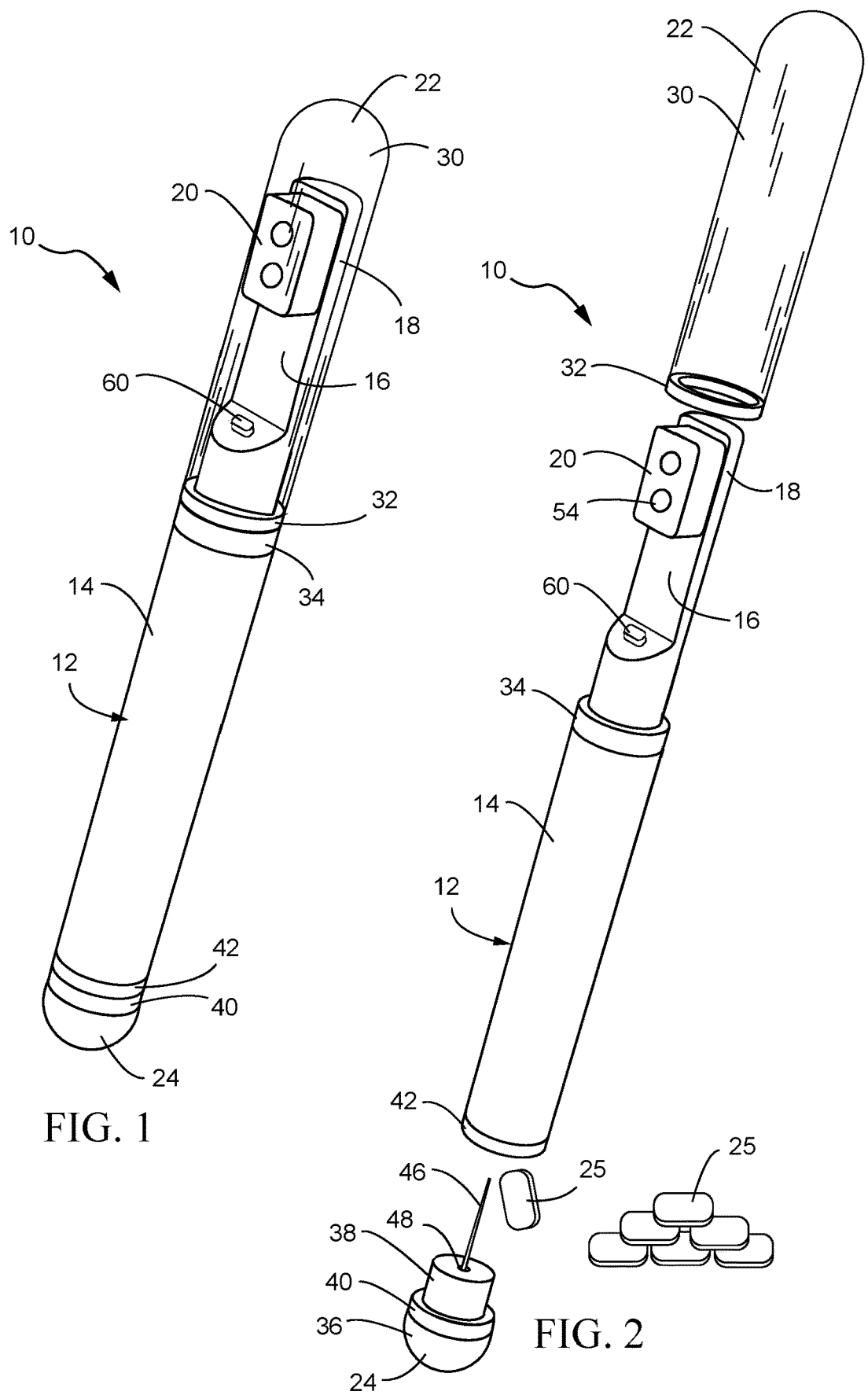

TOOTHBRUSH WITH TOOTHPASTE PELLETS

BACKGROUND

While most toothbrushes are easily portable within a pocket, purse or bag, one must also carry toothpaste. It is not uncommon for travelers to forget to bring toothpaste or to run out of toothpaste when traveling. It is also inconvenient to have to separately carry a tube of toothpaste. While there are toothbrush holders or carrying cases that will hold a toothbrush with a small tube of toothpaste, it is often inconvenient to remove the toothbrush from the carrying case, remove the toothpaste from the carrying case, remove the cap from the toothpaste, apply the toothpaste to the toothbrush, and then reattach the cap to the toothpaste, before being able to actually brush one's teeth, and then reassemble the carrying case with the toothbrush and the toothpaste when done brushing. Accordingly, there remains a need for a toothbrush which is easily portable within a pocket, purse or bag and which self-contains toothpaste, and which is convenient and easy to use at any time and in any location.

BRIEF DESCRIPTION OF THE DRAWINGS

FIG. 1 is a perspective view of one embodiment of a toothbrush.

FIG. 2 is an exploded perspective view of the toothbrush of FIG. 1 showing the removable head cap, the removable handle cap and showing the toothpaste pellets for insertion into the handle portion of the toothbrush.

DESCRIPTION

Figure 3:
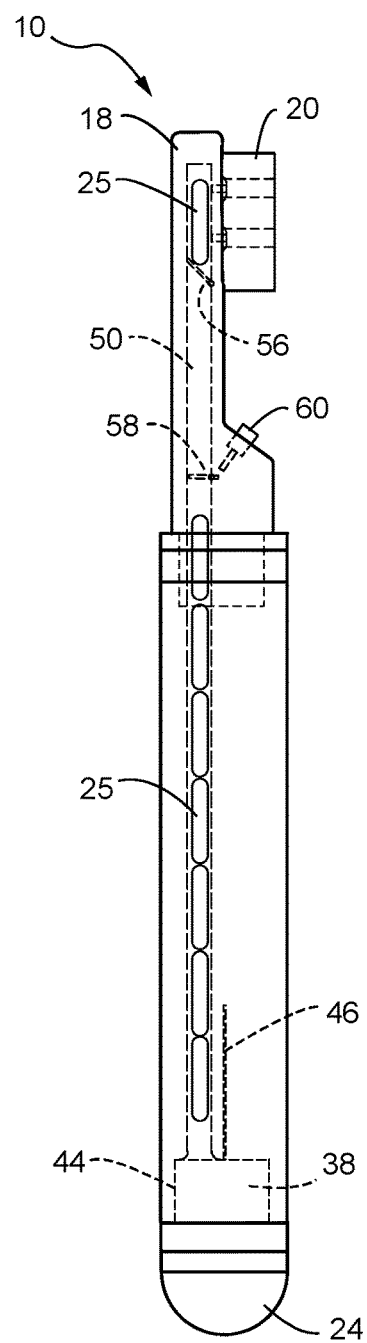
FIG. 3 is a side elevation view of the toothbrush of FIG. 1 with the head cap removed and showing an embodiment of the internal passage in which the toothpaste pellets are received.

Referring now to the drawing figures wherein like reference numbers designate the same or corresponding parts throughout the several views, FIG. 1 is a perspective view of one embodiment of a toothbrush 10 comprising a main body 12, having a handle portion 14, a shank or neck portion 16 and a head portion 18 having brush bristles 20. As best viewed in the exploded perspective view of FIG. 2, the toothbrush 10 includes a removable head cap 22 and a removable handle cap 24. As will be described in more detail later, the toothbrush 10 is adapted for use with toothpaste pills or pellets 25 that are received within the handle portion 14 upon removal of the handle cap 24. During use, one toothpaste pellet 25 is retained within the head portion 18 and, as described later, will foam out through the brush bristles 20 when exposed to water or saliva. The removable head cap 22 protects the head 18 and brush bristles 20 from being soiled during travel and also serves to prevent the wet bristles (and any remaining toothpaste if water is not available to thoroughly rinse the bristles) from dripping or contacting other items when being packed for travel or when being placed in a pocket, purse or bag.

The head portion 18, the brush bristles 20, the shank 16 and handle 14 of the toothbrush 10 may have any desired shape or configuration for aesthetic, ergonomic or utilitarian purposes. Thus it should be appreciated that that shape and configuration of the toothbrush 10 as illustrated in the drawing figures is but one non-limiting example provided for illustration purposes only. It should also be appreciated that although the toothbrush 10 is illustrated as a manual toothbrush, the features and advantages hereinafter described may be incorporated into an electric or battery operated toothbrush, although one of the features or advantages of a manual toothbrush is that it is compact, lightweight and is readily available for use at any time and in any location, without the need for batteries or charging and regardless of whether water or electricity is available.

In one embodiment, both the head cap 22 and the handle cap 24 may be removably secured to the handle portion 14 by a threaded connection, friction fit, a magnetic connection, or any other desired means of removable attachment or any combination thereof. In the embodiment shown, a magnetic connection is utilized for securing both the head cap 22 and the handle cap 24 to the handle portion 14.

In the embodiment shown, the head cap 22 includes a cap casing 30 having a bottom ring 32 made of ferromagnetic material. The bottom ring 32 mates with and magnetically couples to an upper magnetic ring 34 secured to the upper end of the handle portion 14 when the head portion 18 and shank portion 16 are received within the cap casing 30. Similarly the handle cap 24 includes a handle cap body 36 having a plug projection 38 which is surrounded by an upper ring 40 made of ferromagnetic material. The upper ring 40 mates with and magnetically couples to a lower magnetic ring 42 secured to the lower end of the handle portion 14 when the plug projection 38 is received within a mating recess 44 (FIG. 3) within the lower end of the handle portion 14. In embodiments utilizing a threaded connection for the head cap 22 and handle cap 24, the upper end of the handle portion 14 may have external threads and the lower end of the cap casing 30 may have mating internal threads or vice versa. Similarly, for a threaded connection for the handle cap 24, the lower end of the recess 44 may have internal threads that matingly receive external threads on the plug projection 38 or vice versa. In embodiments utilizing a friction fit, the upper and of the handle portion 14 is sized to frictionally receive the lower end of the cap casing 30 or vice versa. Similarly, for a friction fit for the handle cap 24, the recess 44 is sized to frictionally receive the plug projection 38 or vice versa.

The cap casing 30 may be made of transparent or opaque plastic, or the cap casing 30 may be made of metal or any other suitable material. If the cap casing 30 is made of ferromagnetic material, the bottom ring 32 may be omitted. Similarly, the handle cap body 36 may be made of transparent or opaque plastic, or the handle cap body 36 may be made of metal or any other suitable material. If the handle cap body 36 is made of ferromagnetic material, the upper ring 40 may be omitted.

As an additional feature, the handle cap body 36 may incorporate a toothpick 46 (FIGS. 2 and 3). In the embodiment shown, the plug projection 38 includes an aperture 48 in its upper end to frictionally receive and retain one end of the toothpick 46 with the other end of the toothpick 46 received within a cavity within the handle portion 14. The toothpick 46 may be made of any suitable materials such as plastic, natural materials such as wood and may be removable from the aperture 48 for replacement or during use.

Figure 4:
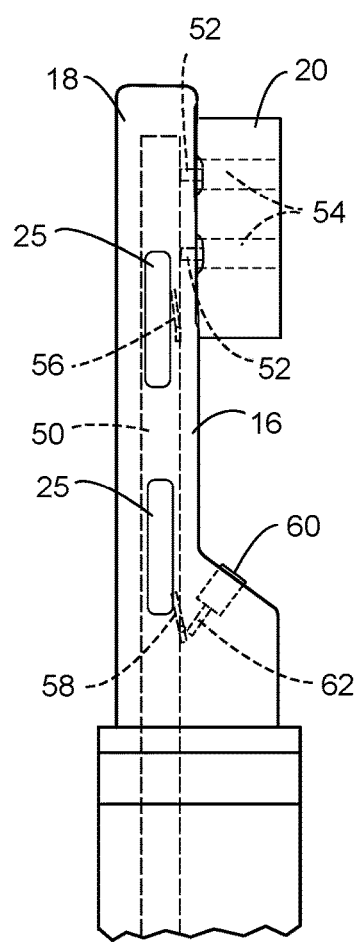
FIG. 4 is an enlarged view of the head portion of FIG. 3 showing the loading of the toothpaste pellets in the head portion.
Figure 5:
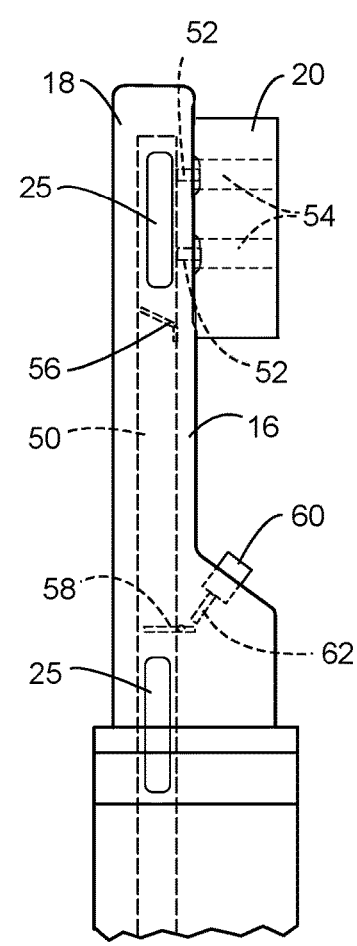
FIG. 5 is the same view as FIG. 4, but showing a toothpaste pellet loaded within the head portion and ready for use.

Referring to FIGS. 3-5, a channel 50 extends through the handle portion 14, the shank portion 16 and into the head portion 18. The head portion 18 includes apertures 52 through its wall toward the brush bristles 20. The brush bristles 20 may include open areas 54 (FIGS. 1 and 2) surrounding the apertures 52. The toothpaste pellets 25 are inserted into the channel 50 while the handle cap 24 is removed from the handle portion 14. In FIG. 3, seven toothpaste pellets 25 are shown received within the channel 50 within the handle portion 14 and an eighth toothpaste pellet 25 is shown within the channel 50 in the head portion 18, behind the brush bristles 20.

As best shown in FIGS. 4 and 5, a one-way head gate 56 and a one-way shank gate 58 are disposed within the channel 50 to control movement of the toothpaste pellet 25 within the channel 50. The one-way head gate 56 is positioned in the channel 50 toward the head portion 18 to retain one toothpaste pellet 25 within the head portion 18 behind the apertures 52 and brush bristles 20 during use. The one-way head gate 56 is configured to move from a normally closed position (FIG. 5) to an open position (FIG. 4). The one-way head gate 56 may be made of a flexible material that will bend or flex or otherwise open to permit the toothpaste pellet 25 to pass through the channel 50 from the shank portion 16 into the head portion 18. Once the toothpaste pellet 25 passes into the head portion 18, the one-way head gate 56 returns to its normally closed position (FIG. 5). The one-way head gate 56 will preferably substantially seal the channel 50 below the one-way head gate 56 to prevent or minimize water, saliva or the toothpaste foam (described later) from passing downward through the channel 50 toward the other toothpaste pellet 25 retained in the channel 50 in the handle portion 14.

The one-way shank gate 58 may be similarly constructed and may similarly function like the one-way head gate 56. Alternatively, the one-way shank gate 58 may be actuated by a push-button 60 to move between a normally closed position (FIG. 5) to an open position (FIG. 4). For example, the push-button 60 may include an inwardly extending rod 62 surrounded by a spring or other suitable biasing means 64 which biases the push-button 60 outwardly. The inward end of the rod 62 may abut an edge of the one-way shank gate 58. When the push-button 60 is pushed inwardly (FIG. 4) the spring 64 is compressed and the inward end of the rod 62 engages with the edge of the one-way shank gate 58 forcing it upwardly to the open position as shown in FIG. 4. When the push-button 60 is released, the spring or biasing means returns the push-button 60 to its original position and the one-way shank gate 58 returns to its normally closed position. The one-way shank gate 58 will preferably further seal the channel 50 below the one-way shank gate 58 to prevent or minimize water, saliva or the toothpaste foam (described later) from passing downward through the channel 50 toward the other toothpaste pills 25 retained the channel 50 in the handle portion 14. The foregoing is but one non-limiting example of the construction and operation of a push-button-actuated one-way shank gate. Any other one-way gate construction or configuration, whether bush-button actuated or via some other mechanism, may serve the intended purpose equally or better than that described above.

With the above-described embodiment, to load the toothpaste pill 25 into the head portion 18 prior to brushing one's teeth, the user grasps the handle portion 14 in one hand pushes the push-button 60 inwardly with his or her thumb to open the one-way shank gate 58. With the one-way shank gate 58 held in the open position, and with the toothbrush firmly grasped in the hand of the user, the user may make an abrupt, downward, jerking motion to force the toothpaste pellets 25 upwardly through the channel 50 toward the head portion 18. The abrupt, downward, jerking motion will cause the upper-most toothpaste pellet 25 to force itself through the one-way head gate 56 and pass into the head portion 18. One the upper-most toothpaste pellet 25 passes into the head portion 18, the one-way head gate 56 will quickly move back to its normally closed position trapping the upper-most toothpaste pellet 25 within the head portion 18 behind the bristles 20. The remaining toothpaste pellets 25 with the channel 50 will slide back into the handle portion 14 through the open one-way shank gate 58, whereupon the user releases the push-button 60 trapping and sealing the remaining toothpaste pellets 25 within the channel 50 in the handle portion 14 below the closed one-way shank gate 58.

Once a toothpaste pellet 25 is loaded within the head portion 18 as described above, the user may then run the brush bristles 20 under water (if available) or simply place the head portion 18 into his or her mouth and begin to brush in the normal manner. The toothpaste pellets 25 are formulated to effervesce when exposed to water or saliva. It should be appreciated that water or saliva will pass through the apertures 52 in the head portion 18 causing the toothpaste pellet 25 trapped behind the brush bristles 20. As the toothpaste pellet 25 begins to effervesce, the bubbles or foam will extrude out through the apertures 52 and through the openings 54 in the brush bristles 20 allowing the user to brush his or her teeth in the same manner as if the user applied toothpaste directly to the brush bristles 20 in the normal manner. Once the toothpaste pellet 25 has finished effervescing and/or the user has completed brushing, the brush bristles may be rinsed (if water is available) and the head cap may be replaced 22, or, if water to rinse the brush bristles 20 is not available, the user may simply replace the head cap 22 to protect the brush bristles from being soiled and to prevent the wet bristles and any remaining toothpaste from dripping or contacting other items when being packed for travel or when being placed in a pocket, purse or bag.

It should be appreciated that the toothpaste pellets 25 are sized and configured to be slidably received within the channel 50. The toothpaste pellet s 25 and the one-way head gate 56 are also preferable sized and positioned so that only one toothpaste pellet 25 at a time is receivable within the head portion 18 above the one-way head gate 56, to ensure that once one toothpaste pill 25 passes into the head portion 18, the one-way head gate 56 will immediately close and substantially seal the channel 50.

The head portion 18 and the shank portion 16 may be made of any suitable material, including plastic or natural materials, such as bamboo, wood or other natural materials as is known in the art. Likewise the brush bristles 20 may be made of any suitable materials, such as nylon or natural fibers, such as bamboo, boar hair other natural fibers as is known in the art. The toothbrush 10 may also be configured such that the head portion 18 with the integrated shank portion 16 are removable from the handle portion 14 for replacement. In that way, if the brush bristles 20 become worn, only the head portion 18 with the integrated shank portion 16 needs to be replaced. In one such embodiment as shown in FIG. 3, the lower end of the shank portion 16 may include external threads that are threadably received by internal threads within an upper cavity 66 of the handle portion 14 or vice versa. In such an embodiment, an alignment guide, such as a marking or a flattened surface (not shown) may be provided on the shank portion 16 and on the handle portion 14 for ensuring proper alignment of the channel 50 within the shank portion 16 and the channel 50 within the handle portion 14.

The formulation of the toothpaste pellets 25 may include fluoride, glycerol or glycerin, sorbitol, calcium carbonate and sodium lauryl sulfate. Sodium fluoride, sodium monofluorophosphate and stannous fluoride are the three types of fluoride recognized by the FDA for cavity prevention. Glycerol or glycerin retains moisture and may help to hold the toothpaste pill together and may assist in the toothpaste pellets sliding through the channel 50. Sorbitol acts as a sweetening agent and may also help to hold the toothpaste pellets together. Instead of sorbitol, saccharin may be used as a sweetening agent. Calcium carbonate acts as abrasive to help with removal of plaque, debris and teeth stains. Other suitable abrasives may include dehydrated silica gels, hydrated aluminum oxides, magnesium carbonate, phosphate salts and silicates. Sodium lauryl sulfate is a foaming agent. Other suitable foaming agents, may include sodium N-Lauryl sarcosinate.

The foregoing description and drawings are intended to be illustrative and not restrictive. Various modifications to the embodiments and to the general principles and features of the system and methods described herein will be apparent to those of skill in the art. Thus, the disclosure should be accorded the widest scope consistent with the appended claims and the full scope of the equivalents to which such claims are entitled.

The invention claimed is:

1. A toothbrush, comprising:
   a head portion having brush bristles;
   a shank portion;
   a handle portion;
   a channel extending longitudinally through the handle portion, the shank portion and terminating in the head portion, the channel sized to slidably receive a plurality of toothpaste pellets within the handle portion;
   an aperture extending transverse through the head portion and providing fluid communication into the channel;
   a first one-way head gate disposed within the channel above the handle portion and at a distance relative to the head portion such that only an upper most one of the plurality of toothpaste pellets within the channel is receivable within the head portion, the first one-way gate configured to move between a normally closed position and an open position;
   a handle cap adapted to removably attach to a lower end of the handle portion, whereby when attached to the lower end of the handle portion, the handle cap closes a lower end of the channel extending through the handle portion
   whereby, the one-way head gate is movable between the normally closed position and the open position by a user grasping the handle portion and making an abrupt, downward, jerking motion, whereupon the plurality of toothpaste pellets are forced upwardly through the channel from the handle portion and into the shank portion toward the head portion, and whereupon the upper-most one of the plurality of toothpaste pellets forces the one-way head gate to move from the normally closed position to the open position such that the upper-most one of the plurality of toothpaste pellets passes from the shank portion into the head portion, and whereupon the one-way head gate again moves to the normally closed position trapping the upper-most one of the plurality of toothpaste pellets within the head portion behind the brush bristles above the one-way head gate and wherein any remaining ones of the plurality of toothpaste pellets fall back through the channel from the shank portion and into the handle portion.

2. The toothbrush of claim 1, further comprising:
   a head cap adapted to receive the head portion and the shank portion and removably attach to an upper end of the handle portion.

3. The toothbrush of claim 2, wherein one of a lower end of the head cap and the upper end of the handle portion include a ferromagnetic ring and one other of the lower end of the head cap and the upper end of the handle portion includes a magnet to magnetically couple the lower end of the head cap with the upper end of the handle portion.

4. The toothbrush of claim 2, wherein a lower end of the head cap and the upper end of the handle portion include mating threads to threadably attach the lower end of the head cap with the upper end of the handle portion.

5. The toothbrush of claim 2, wherein a lower end of the head cap and the upper end of the handle portion are sized to frictionally couple the lower end of the head cap with the upper end of the handle portion.

6. The toothbrush of claim 1, wherein one of an upper end of the handle cap and the lower end of the handle portion include a ferromagnetic ring and one other of the upper end of the handle cap and the lower end of the handle portion includes a magnet to magnetically couple the handle cap with the lower end of the handle portion.

7. The toothbrush of claim 1, wherein an upper end of the handle cap and the lower end of the handle portion include mating threads to threadably attach the handle cap with the lower end of the handle portion.

8. The toothbrush of claim 1, wherein an upper end of the handle cap and the lower end of the handle portion are sized to frictionally couple the handle cap with the lower end of the handle portion.

9. The toothbrush of claim 1, further comprising a one-way shank gate disposed within the channel below the one-way head gate, the one-way shank gate configured to move between a normally closed position and an open position;
   whereby the one-way shank gate is movable between the normally closed position and the open position by the user actuating the one-way shank gate to move from the normally closed position to the open position before making the abrupt, downward, jerking motion, such that the plurality of toothpaste pellets are capable of moving through the channel from the handle portion into the shank portion.

10. The toothbrush of claim 1, wherein the toothpaste pellet is formulated to effervesce when exposed to water or saliva.

* * * * *